United States Patent
Karamanoglu et al.

(10) Patent No.: US 7,470,233 B2
(45) Date of Patent: Dec. 30, 2008

(54) METHOD AND APPARATUS FOR MUSCLE FUNCTION MEASUREMENT

(75) Inventors: Mustafa Karamanoglu, Fridley, MN (US); Vincent E. Splett, Apple Valley, MN (US); Tommy D. Bennett, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

(21) Appl. No.: 11/043,819

(22) Filed: Jan. 26, 2005

(65) Prior Publication Data

US 2006/0167358 A1  Jul. 27, 2006

(51) Int. Cl.
*A61B 5/02* (2006.01)
(52) U.S. Cl. ...................... 600/485; 600/587
(58) Field of Classification Search ................ 600/485, 600/486, 300, 324, 325, 333, 335, 341, 345, 600/348, 373, 374, 377, 508, 561, 488, 513, 600/515–518, 510, 587; 607/6, 7, 17, 19, 607/23, 24, 4, 5, 9, 119, 121–123; 128/903; 604/67, 288.01, 93.01
See application file for complete search history.

(56) References Cited

U.S. PATENT DOCUMENTS

| | | | |
|---|---|---|---|
| 3,815,611 A | | 6/1974 | Denniston, III |
| 4,485,813 A | | 12/1984 | Anderson et al. |
| 4,566,456 A | * | 1/1986 | Koning et al. ................ 607/23 |
| 4,936,304 A | | 6/1990 | Kresh et al. |
| 5,129,394 A | * | 7/1992 | Mehra ......................... 607/23 |
| 5,271,392 A | | 12/1993 | Ferek-Petric |
| 5,368,040 A | * | 11/1994 | Carney ........................ 600/513 |
| 5,417,717 A | * | 5/1995 | Salo et al. ..................... 607/18 |
| 5,496,351 A | * | 3/1996 | Plicchi et al. ................. 607/17 |
| 5,564,434 A | * | 10/1996 | Halperin et al. ............. 600/488 |
| 5,693,074 A | | 12/1997 | Ferek-Petric |
| 5,743,267 A | * | 4/1998 | Nikolic et al. ............... 600/483 |
| 5,758,652 A | | 6/1998 | Nikolic et al. |

(Continued)

FOREIGN PATENT DOCUMENTS

WO    WO 02/053228 A1 *   7/2002

OTHER PUBLICATIONS

Grossman et al., "new Technique for Determining Instantaneous Myocardial Force-Velocity Relations in the Intact Heart", Circulation Research, vol. 28, 1971, pp. 290-297.

(Continued)

*Primary Examiner*—Charles A Marmor, II
*Assistant Examiner*—Anita Saidi
(74) *Attorney, Agent, or Firm*—Stephen W. Bauer

(57) ABSTRACT

The present invention provides an apparatus and method for monitoring muscle function based on an index derived from a pressure or force signal. The muscle function index is derived from an instantaneous muscle stiffness ratio computed as the ratio of the first time derivative of the pressure or force waveform to the corresponding instantaneous pressure or force. The instantaneous stiffness ratio, $\dot{E}/E(t)$, is in units of 1/sec and relates to the rate of strong bond formation and will be influenced by calcium handling properties of the muscle fibers and the intracellular calcium concentration. As such, an index derived from $\dot{E}/E(t)$ provides a measure of the inotropic status of the muscle.

21 Claims, 6 Drawing Sheets

U.S. PATENT DOCUMENTS

| | | | |
|---|---|---|---|
| 5,800,464 A * | 9/1998 | Kieval | 607/9 |
| 6,438,408 B1 * | 8/2002 | Mulligan et al. | 600/510 |
| 6,795,732 B2 * | 9/2004 | Stadler et al. | 607/17 |
| 6,915,162 B2 * | 7/2005 | Noren et al. | 607/23 |
| 6,939,303 B2 * | 9/2005 | Curiel | 600/481 |
| 2002/0138009 A1 * | 9/2002 | Brockway et al. | 600/485 |
| 2003/0092998 A1 | 5/2003 | Curiel | |
| 2004/0215049 A1 * | 10/2004 | Zdeblick et al. | 600/16 |
| 2004/0220638 A1 | 11/2004 | Mulligan et al. | |
| 2005/0182330 A1 * | 8/2005 | Brockway et al. | 600/486 |

OTHER PUBLICATIONS

Mirsky et al., "Coreection for preload in assessment of mycardial contractility in aortic and mitral valve disease. Application of the concept of systolic myocardial stiffness", Circulation, vol. 78, 1988 pp. 68-80.

Quinones et al., "Influence of acute changes in preload, afterload, contractile state and heart rate on ejection and isovolumic indices of mycardial contractility in man", Circulation, vol. 53, No. 2, Feb. 1976, pp. 293-302.

"Assessment of Cardiac Contractility; The Relation Between the Rate of Pressure Rise and Ventricular Pressure During Isovolumic Systole," Circulation, vol. 44, pp. 47-58 (1971).

* cited by examiner

METHOD AND APPARATUS FOR MUSCLE FUNCTION MEASUREMENT

FIELD OF THE INVENTION

The present invention relates generally to an apparatus and method for monitoring muscle function and more particularly a method for deriving an index of muscle function from monitoring muscular pressure or force.

BACKGROUND OF THE INVENTION

The contractile status of a muscle can be assessed by measuring the force-length relationship, or pressure-volume relationship in the case of cardiac muscle. Generally, measurement of this relationship requires instantaneous measurements of force and length, or pressure and volume, simultaneously. The contractile status of cardiac muscle can be computed as the instantaneous stiffness, E(t), which is the ratio of the instantaneous developed pressure P(t) to the associated change in ventricular volume (V(t)-$V_o$). The contractile status of skeletal muscle can be computed as the instantaneous stiffness, K(t), equal to the ratio the instantaneous developed force F(t) to the associated change in length (L(t)-$L_o$). These ratios are related to the calcium cycling of the muscle fibers and formation of strong bonds between myofilaments.

Obtaining instantaneous force and length or pressure and volume measurements directly is generally an invasive procedure that is not technically convenient or easily performed. As such, measurements for assessing the contractile status of skeletal muscle, the heart or other muscular organ are not widely used in clinical diagnosis, monitoring of a medical condition, or managing medical treatment. Information regarding the contractility or inotropic state of a muscle would be valuable to a clinician in managing medical treatment.

In general, contractility refers to the amount of force or pressure a muscle generates at a given resting length or preload. Changes in contractility reflect changes in the inotropic state of the muscle. The inotropic state can be altered by disease. Hemodynamic performance of the heart depends on the preload (the ventricular end-diastolic fiber length), the afterload, and the inotropic state of the myocardium. Hemodynamic evaluation often includes measurements of ejection fraction, stroke volume, and systolic and diastolic pressures and volumes which are affected by changes in ventricular contractility but are also influenced by changes in preload and afterload. Such measures therefore do not provide an assessment of ventricular contractility independent of influences of afterload and preload. Indices of myocardial function can be derived from methods such as obtaining pressure-volume loops and determining end-systolic pressure-volume relationships or preload recruitable stroke work. However, these methods are complicated, time-consuming and require considerable skill.

BRIEF SUMMARY OF THE INVENTION

The present invention provides an apparatus and method for monitoring muscle function based on an index derived from a pressure or force signal, without requiring the simultaneous volume or length measurement. The muscle function index is derived from an instantaneous muscle stiffness ratio computed as the ratio of the first time derivative of the pressure or force waveform to the instantaneous pressure or force. The instantaneous stiffness ratio, $\dot{E}/E(t)$, is in units of 1/s and relates to the rate of strong bond formation and will be influenced by calcium handling properties of the muscle fibers and the intracellular calcium concentration. As such, an index derived from $\dot{E}/E(t)$ provides a measure of the inotropic status of the muscle.

In one embodiment, the apparatus includes a pressure sensor adapted for implantation at a location appropriate for measuring pressure developed within a chamber of a muscular organ, such as in an atrial or ventricular chamber of the heart, during muscular contraction. In another embodiment, the apparatus includes a pressure sensor adapted for implantation within muscular tissue for measuring intramuscular pressure developed during muscular contraction. The pressure sensor is coupled to a sensor interface for receiving a pressure signal and transferring the pressure signal, in an analog or digital format, to processing circuitry. Processing circuitry analyzes the pressure signal to compute the instantaneous stiffness ratio $\dot{E}/E(t)$ and derive the muscle function index therefrom.

The sensor interface and processing circuitry may be included in an implantable medical device that provides patient monitoring functionality and, in some embodiments, may include therapy delivery. In other embodiments, the sensor interface and processing circuitry may be included in an external monitoring and/or therapy delivery unit.

In another embodiment, the apparatus includes a force transducer that is adapted for coupling to muscle tissue, directly or indirectly, for measuring muscular force generated during contraction. A sensor interface and processing circuitry are used for deriving the muscle function index from the instantaneous stiffness ratio computed as a function of force rather than pressure.

In an associated method, the first derivative of the pressure (or force) signal is computed for at least the isovolumic or isometric portion of a contraction cycle. The first time derivative of the pressure or force signal is divided by the instantaneous pressure (or force) to obtain a $\dot{E}/E(t)$ waveform. The muscle function index is derived from the $\dot{E}/E(t)$ waveform as a selected feature of the $\dot{E}/E(t)$ waveform, such as the peak, width, area, or slope. The index may be stored over time to allow trend assessments of muscle function for monitoring a disease state or therapy response. The index may further be used as feedback in therapy control algorithms.

In another embodiment, the first derivative of the pressure (or force) signal is computed for the relaxation phase of a contraction cycle. A plot of $\dot{E}/E(t)$ computed as the first derivative of the pressure (or force) divided by the instantaneous pressure (or force) during the relaxation phase allows for derivation of a muscle function index relating to the relaxation properties of the muscle. The index derived from the relaxation phase of the $\dot{E}/E(t)$ plot will relate to the dissociation of strong bonds and calcium sequestration.

DETAILED DESCRIPTION

Figure 1:
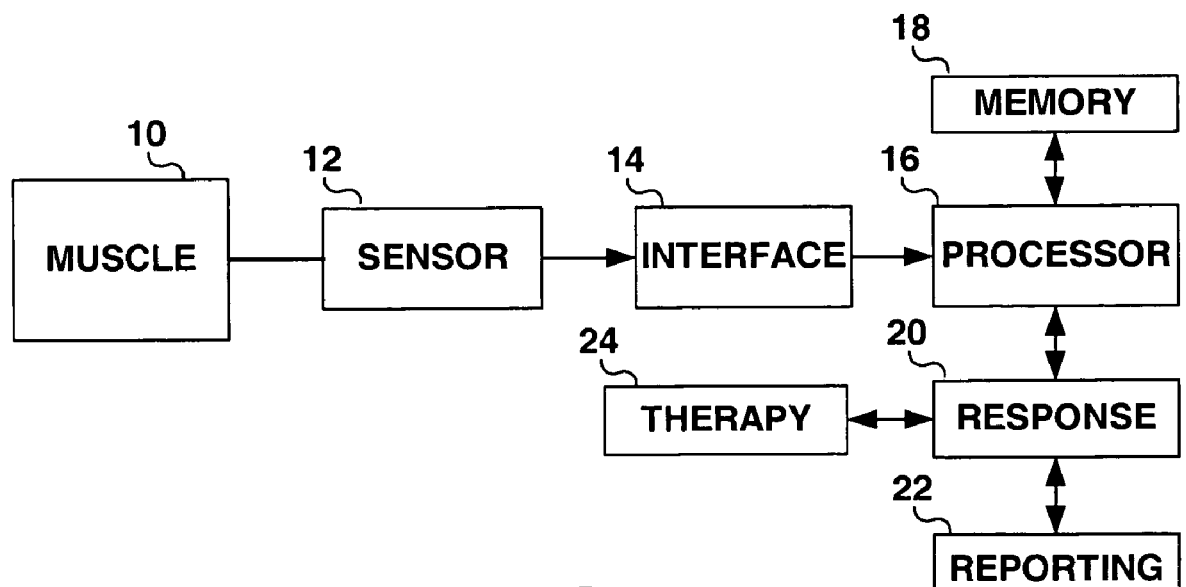
FIG. 1 illustrates a functional block diagram providing an overview of a system for monitoring muscle function.

FIG. 1 illustrates a functional block diagram providing an overview of a system for monitoring muscle function. A sensor 12 is positioned for monitoring the function of a muscle, muscle group or muscular organ 10. Sensor 12 is a pressure sensor or a force transducer positioned to measure the pressure or force generated by muscle 10 during a contraction. A pressure sensor may be implanted in a chamber of a hollow muscular organ, such as within a heart chamber, for monitoring pressure developed by contraction of the muscular organ. A pressure sensor may alternatively be implanted within the muscle tissue, for example within skeletal muscle tissue or within the heart wall, for measuring intramuscular pressure developed during contraction. A force transducer may be coupled directly to muscle tissue or indirectly to muscle tissue via a tendon, myofascial tissue, bone, other element subjected to force generated by the muscle tissue contraction.

Sensor 12 is coupled to a sensor interface 14 for receiving the pressure or force signal from sensor 12 and providing the signal to processing circuitry 16. Interface 14 may include various signal conditioning circuitry, such as a filter, amplifier, analog-to-digital converter, or the like, for conditioning the raw sensor signal for processing by processor 16. Processor 16 may be embodied as a microprocessor with associated memory 18. Processor 16 receives the sensor signal from interface 14 and executes algorithms stored in memory 18 to derive a muscle function index from the sensor signal. Alternatively, processor 16 may be embodied as dedicated analog or digital circuitry for performing the mathematical functions for deriving the muscle function index from the pressure or force signal.

The derived index can be stored in memory 18 such that trends in the index over time or in response to various interventions can be evaluated. The derived index may further be used to provide a response according to a response module 20. The response module 20 controls activation of an appropriate response to a derived muscle function index value. Responses may include generating a report by reporting module 22 or delivering, altering or withholding a therapy by therapy delivery module 24.

Reporting module 22 is any circuit or routine capable of producing appropriate feedback from the IMD to the patient or to a physician. In various embodiments, suitable reports might include storing data in memory 18, generating an audible or visible alarm, or producing a message for display or for transmission via a communication link or network.

Therapy delivery module 24 is any device or unit capable of delivering a medical therapy such as a drug delivery pump or an electrical pulse generator. Various delivered therapies that may be provided, altered or withheld in response to a derived muscle function index include, but are not limited to, a drug delivery; cardiac stimulation, for example in the form of pacing, resynchronization therapy, extra systolic stimulation, or anti-arrhythmia therapy; neural stimulation, or muscular stimulation.

The functionality summarized in FIG. 1 may be implemented in an implantable medical device system that includes an implantable sensor and implantable medical device (IMD) for acquiring pressure or force data and processing such data for deriving a muscle function index. The IMD may store muscle function index data such that it can be transmitted to an external device via telemetry for review and analysis by a clinician. The IMD may also deliver a therapy in response to a derived index or alter a delivered therapy.

In various embodiments, muscle function monitoring according to the present invention may be implemented in any IMD capable of monitoring a pressure or force signal including, by not limited to: an implantable pulse generator, which may be used for delivering functional electrical stimulation to restore muscular function for mobility, continence, or other functionality; neurological stimulators, which may be used for affecting parasympathetic/sympathetic activity or influencing neuromuscular function; a drug pump; or a cardiac stimulation device such as a pacemaker or cardioverter/defibrillator. Alternatively, the functionality summarized in FIG. 1 may be implemented in any external medical device system that includes a sensor adapted for positioning relative to muscle tissue to provide muscle function monitoring. The external medical device may also provide therapy delivery. In some embodiments, the functionality described may be implemented across one or more implantable and/or external devices to provide muscle function monitoring and appropriate responses to derived muscle function indices.

Figure 2:
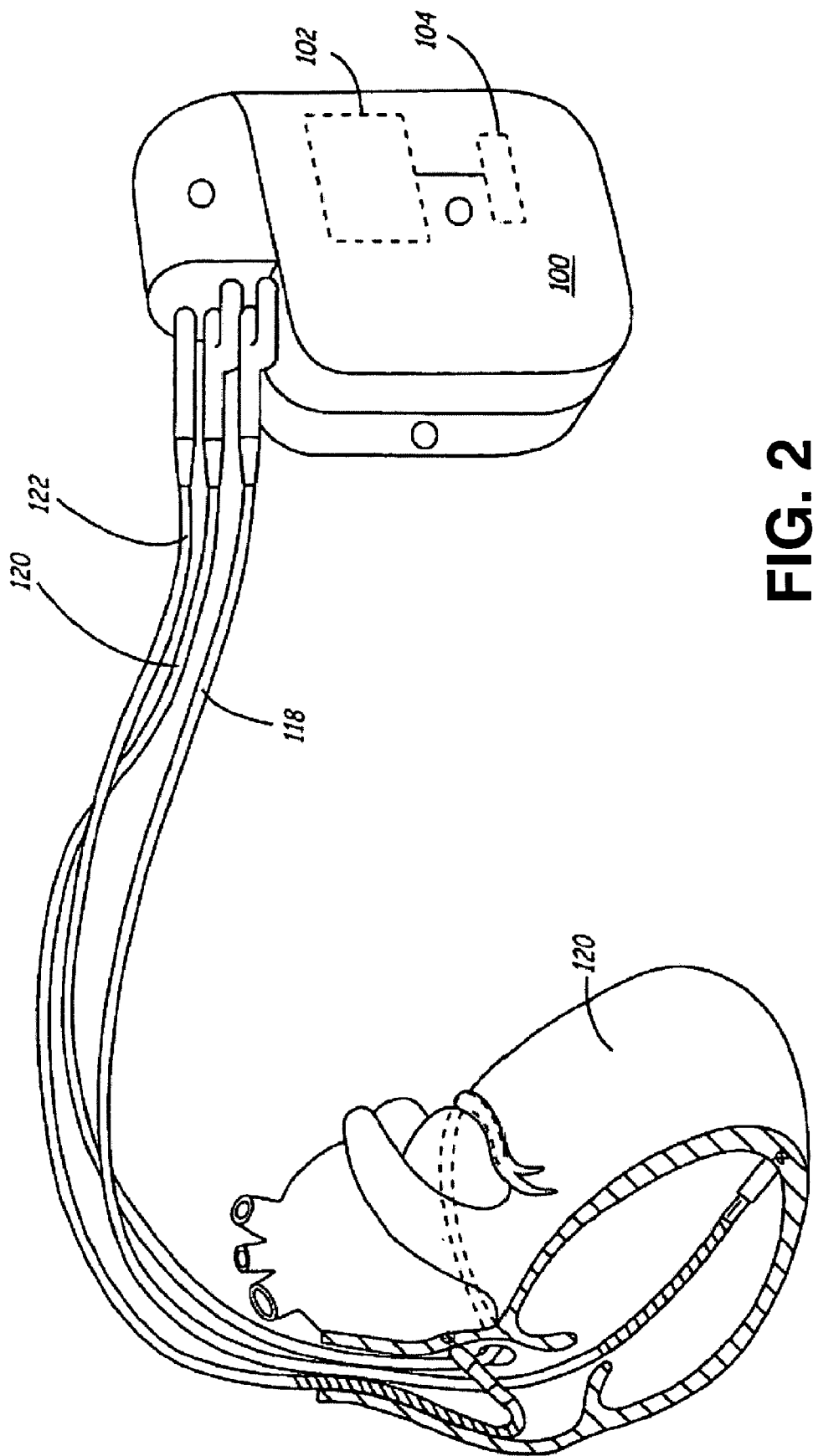
FIG. 2 illustrates an exemplary implantable medical device (IMD) connected to monitor a patient's heart.

FIG. 2 is an illustration of an exemplary implantable medical device (IMD) 100 connected to monitor a patient's heart 120, including monitoring myocardial function in accordance with the present invention. IMD 100 will be described in detail as one exemplary device in which the present invention may be implemented for monitoring muscle function, in this case myocardial function in particular. IMD 100 may be configured to integrate both monitoring and therapy features, as will be described below. IMD 100 collects and processes data about heart 120 from one or more sensors including a pressure sensor and an electrode pair for sensing cardiac electrogram (EGM) signals. As shown in FIG. 2, IMD 100 may be generally flat and thin to permit subcutaneous implantation within a human body, e.g., within upper thoracic regions or the lower abdominal region. IMD 100 is provided with a hermetically-sealed housing that encloses a processor 102, a digital memory 104, and other components as appropriate to produce the desired functionalities of the device. In various embodiments, IMD 100 is implemented as any implanted medical device capable of measuring the heart rate of a patient and a ventricular or atrial pressure signal, or an intramyocardial pressure signal, including, but not limited to, a pacemaker, defibrillator, electrocardiogram monitor, blood pressure monitor, drug pump, insulin monitor, or neurostimulator. An example of a suitable IMD that may be used in various exemplary embodiments is the CHRONICLE® monitoring device available from Medtronic, Inc. of Minneapolis, Minn., which includes a mechanical sensor capable of detecting a pressure signal. In a further embodiment, IMD 100 is any device that is capable of sensing a pressure signal and providing pacing and/or defibrillation or other electrical stimulation therapies to the heart. Another example of an IMD capable of sensing pressure-related parameters is described in commonly assigned U.S. Pat. No. 6,438,408B1 issued to Mulligan et al. on Aug. 20, 2002.

Processor 102 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 102 executes instructions stored in digital memory 104 to provide functionality as described below. Instructions provided to processor 102 may be executed in any manner, using any data structures, architecture, programming language and/or other techniques. Digital memory 104 is any storage medium capable of maintaining digital data and instructions provided to processor 102 such as a static or dynamic random access memory (RAM), or any other electronic, magnetic, optical or other storage medium.

As further shown in FIG. 2, IMD 100 may receive one or more cardiac leads for connection to circuitry enclosed within the housing. In the example of FIG. 2, IMD 100 receives a right ventricular endocardial lead 118, a left ventricular coronary sinus lead 122, and a right atrial endocardial lead 120, although the particular cardiac leads used will vary from embodiment to embodiment. In addition, the housing of IMD 100 may function as an electrode, along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and/or defibrillation. In addition, ventricular leads 118 and 122 may deliver pacing stimuli in a coordinated fashion to provide biventricular pacing, cardiac resynchronization, extra systolic stimulation therapy or other therapies. IMD 100 may also obtain input data from other internal or external sources (not shown) such as an oxygen sensor, pH monitor, accelerometer or the like.

IMD 100 obtains pressure data input from a pressure sensor that is carried by a lead extending from IMD 100, such as any of leads 118, 122, and 120, or a separate, independent lead. A pressure sensor may be located on a lead such that upon lead deployment the pressure sensor is located in a desired heart chamber, within the myocardium, or within a cardiac artery or vein as desired to provide a pressure signal that corresponds to pressure generated by the contracting myocardium. In one embodiment, a pressure sensor may be located on right ventricular lead 118 such that, when lead 118 is deployed, the pressure sensor is positioned in the right ventricle, and a right ventricular pressure signal is obtained. In another embodiment, a pressure sensor may be located on coronary sinus lead 122 such that when lead 122 is deployed the pressure sensor is positioned in a cardiac vein over the left ventricle, and a pressure signal relating to left ventricular pressure is obtained. In still another embodiment, a pressure sensor may be located at or near a lead tip such that upon fixation of the lead tip in the myocardial wall, the pressure sensor is positioned to obtain an intramyocardial pressure signal. Pressure sensor and lead configurations may vary widely in various embodiments of the present invention.

In operation, IMD 100 obtains data about heart 120 via leads 118, 120, 122, and/or other sources. This data is provided to processor 102, which suitably analyzes the data, stores appropriate data in memory 104, and/or provides a response or report as appropriate. Any identified cardiac episodes (e.g. an arrhythmia or heart failure decompensation) can be treated by intervention of a physician or in an automated manner. In accordance with the present invention, detection of a cardiac event may involve detection of a change in the muscle function index derived according to the methods described in detail below. In various embodiments, IMD 100 activates an alarm upon detection of a cardiac event. Alternatively or in addition to alarm activation, IMD 100 selects or adjusts a therapy and coordinates the delivery of the therapy by IMD 100 or another appropriate device. Optional therapies that may be applied in response to detection of a cardiac event in various embodiments may include drug delivery or electrical stimulation therapies such as cardiac pacing, resynchronization therapy, extra systolic stimulation, and neurostimulation.

Figure 3:
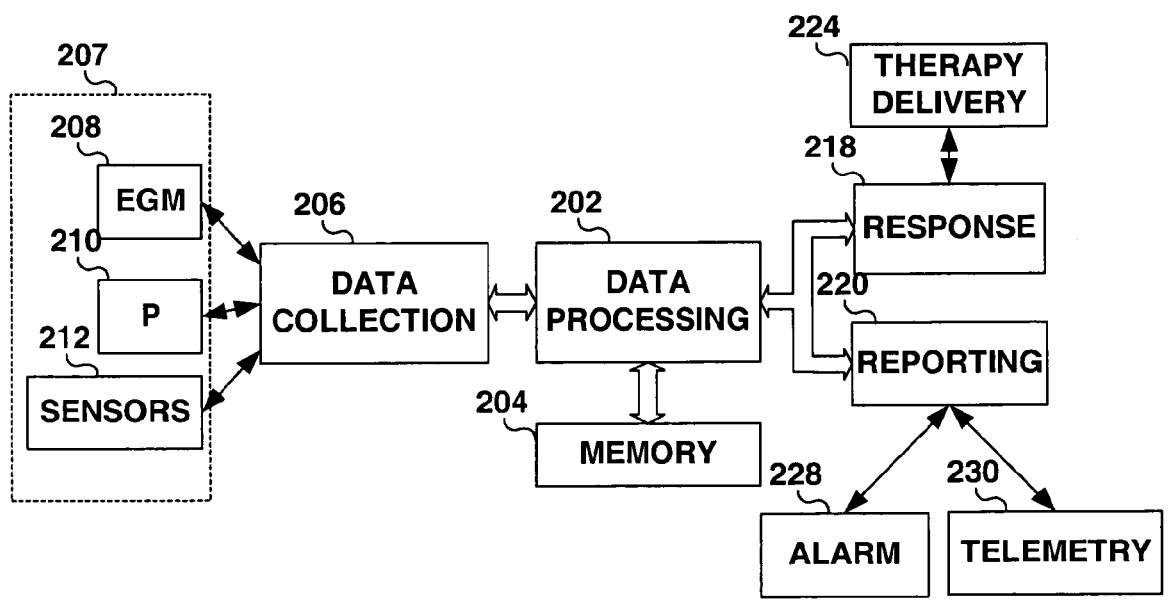
FIG. 3 is a block diagram summarizing the data acquisition and processing functions appropriate for practicing the invention in an IMD, such as the IMD shown in FIG. 2.

FIG. 3 is a block diagram summarizing the data acquisition and processing functions appropriate for practicing the invention in an IMD, such as the IMD 100 shown in FIG. 2. The functions shown in FIG. 3 may be implemented in any IMD system, or alternatively, the functions shown in FIG. 3 may be implemented in an external monitoring system that includes sensors coupled to a patient for acquiring pressure signal data. The system includes a data collection module 206, a data processing module 202, a response module 218 and/or a reporting module 220. Each of the various modules may be implemented with computer-executable instructions stored in memory 104 and executing on processor 102 (shown in FIG. 2), or in any other manner.

The exemplary modules and blocks shown in FIG. 3 are intended to illustrate one logical model for implementing an IMD 100, and should not be construed as limiting. Indeed, the various practical embodiments may have widely varying software modules, data structures, applications, processes and the like. As such, the various functions of each module may in practice be combined, distributed or otherwise differently-organized in any fashion across a patient monitoring system. For example, a system may include an implantable pressure sensor and EGM circuit coupled to an IMD used to acquire pressure and EGM data, an external device in communication with the IMD to retrieve the pressure and EGM data and coupled to a communication network for transferring the pressure and EGM data to a remote patient management center for analysis. Examples of remote patient monitoring systems in which aspects of the present invention could be implemented are generally disclosed in U.S. Pat. No. 6,497,655 issued to Linberg and U.S. Pat. No. 6,250,309 issued to Krichen et al., both of which patents are incorporated herein by reference in their entirety.

Data collection module 206 is interfaced with one or more data sources 207 to obtain data about the patient. Data sources 207 include any source of information about the patient's heart or other physiological signals. Data sources 207 include an ECG or EGM source 208 that provides cardiac electrical signals such as P-waves or R-waves used to monitor the patient's heart rhythm. Data sources 207 further include a pressure sensor 210 for obtaining a pressure signal from which a muscle function index will be computed according to methods described in detail below.

Pressure sensor 210 may be deployed in a ventricle, atrium, within the myocardial tissue, or at any location suitable for obtaining a pressure signal correlated to the pressure generated by myocardial contraction. In some embodiments, pressure sensor 210 may include multiple pressure sensors deployed at different sites to provide multiple pressure signals for use in monitoring myocardial function. Pressure sensor 210 may be embodied as the pressure sensor disclosed in commonly assigned U.S. Pat. No. 5,564,434, issued to Halperin et al., hereby incorporated herein in its entirety.

Data sources 207 may include other sensors 212 for acquiring physiological signals useful in monitoring a cardiac condition such as an accelerometer or wall motion sensor, a blood gas sensor such as an oxygen sensor, a pH sensor, or impedance sensors for monitoring respiration, lung wetness, or cardiac chamber volumes. The various data sources 207 may be provided alone or in combination with each other, and may vary from embodiment to embodiment.

The present invention may be implemented in other IMDs used for monitoring striated muscle, other than cardiac muscle. In various embodiments, the types of signal sources included in sources 207 may vary. For example, when the present invention is embodied as an implantable pulse generator (IPG) for delivering stimulation pulses to skeletal muscle, an electromyogram (EMG) signal source may be provided in place of EGM source 208. Providing an electrical signal of muscle activity, i.e. an EGM signal as shown in FIG. 3 or an EMG signal in other applications, facilitates the timing of pressure or force signal acquisition during a contraction. An electrical signal corresponding to muscle depolarization may be used as an indication of the onset of a contraction and trigger the collection and storage of a pressure or force signal in a memory buffer. An electrical signal corresponding to repolarization may be used for ending the acquisition and storage of a pressure or force signal. The stored signal is then used by data processing 202 in computing an instantaneous stiffness ratio from which a muscle function index is derived.

Data collection module 206 receives data from each of the data sources 207 by polling each of the sources 207, by responding to interrupts or other signals generated by the sources 207, by receiving data at regular time intervals, or according to any other temporal scheme. Data may be received at data collection module 206 in digital or analog format according to any protocol. If any of the data sources generate analog data, data collection module 206 translates the analog signals to digital equivalents using an analog-to-digital conversion scheme. Data collection module 206 may also convert data from protocols used by data sources 207 to data formats acceptable to data processing module 202, as appropriate.

Data processing module 202 is any circuit, programming routine, application or other hardware/software module that is capable of processing data received from data collection module 206. In various embodiments, data processing module 202 is a software application executing on processor 102 of FIG. 2 or another external processor to implement the process described below in conjunction with FIG. 4. Accordingly, data processing module 202 processes pressure signals for computing a muscle function index, as described more fully below.

In an exemplary embodiment, processing module 202 receives data from pressure sensor 210 and EGM data from EGM sensing electrodes 208 from data collection module 206 and interprets the data using analog or digital signal processing techniques to compute a muscle function index on a single cardiac cycle or a beat-by-beat basis. The beat-by-beat muscle function index can be statistically analyzed to determine an average index and trends in the muscle function index. The muscle function index and/or intermediate computational results may be stored in memory 204, which may correspond to hardware memory 104 shown in FIG. 2, or may be implemented with any other available digital storage device.

When a change in heart function based on the muscle function index and/or other hemodynamic signals is detected, processing module 202 may trigger an appropriate response. Responses may be activated by sending a digital message in the form of a signal, passed parameter or the like to response module 218 and/or reporting module 220.

Reporting module 220 is any circuit or routine capable of producing appropriate feedback from the IMD to the patient or to a physician. In various embodiments, suitable reports might include storing data in memory 204, generating an audible or visible alarm 228, producing a wireless message transmitted from a telemetry circuit 230. Reports may include information about the muscle function index and may include heart rhythm information, other physiologic data, time and date of data collection, and any other appropriate data. In a further embodiment, the particular response provided by reporting module 220 may vary depending upon the severity of the cardiac function change. Minor episodes may result in no alarm at all, for example, or a relatively non-obtrusive visual or audible alarm. More severe episodes might result in a more noticeable alarm and/or an automatic therapy response.

When the functionality diagramed in FIG. 3 is implemented in an IMD, telemetry circuitry 230 is included for communicating data from the IMD to an external device adapted for bidirectional telemetric communication with IMD 100. The external device receiving the wireless message may be a programmer/output device that advises the patient, a physician or other attendant of serious conditions, e.g., via a display or a visible or audible alarm. Information stored in memory 204 may be provided to an external device to aid in diagnosis or treatment of the patient. Alternatively, the external device may be an interface to a communications network such that the IMD is able to transfer data to an expert patient management center or automatically notify medical personnel if an extreme episode occurs.

Response module 218 is any circuit, software application or other component that interacts with any type of therapy-providing system 224, which may include any type of therapy delivery mechanisms such as a drug delivery system, neurostimulation, and/or cardiac stimulation. In some embodiments, response module 218 may alternatively or additionally interact with an electrical stimulation therapy device that may be integrated with an IMD to deliver pacing, extra systolic stimulation, anti-tachycardia pacing, cardioversion, defibrillation, vagal stimulation, and/or any other therapy. Accordingly, the various responses that may be provided by the system vary from simple storage and analysis of data to actual provision of therapy in various embodiments. Any therapy provided may be controlled or adjusted in response to a muscle function index change or in response to a combination of physiological signals acquired by data sources 207. Drug dosage may be adjusted according to episode severity, for example, or electrical stimulation parameters can be adjusted in response to observed changes in heart function measures.

In particular, a muscle function index derived from an instantaneous muscle stiffness ratio computed from the pressure source 210 may be used by therapy control algorithms for delivering, adjusting, or withdrawing a drug therapy or an electrical stimulation therapy. For example, if a muscle function index indicates a decline in function, a contractility enhancing agent may be provided or increased. Alternatively, timing intervals or other pacing parameters may be adjusted to optimize dual chamber or bi-ventricular chamber pacing, cardiac resynchronization therapy, extra-systolic stimulation or other pacing therapies in order to improve or maintain an index of myocardial function derived from the instantaneous muscle stiffness ratio.

The various components and processing modules shown in FIG. 3 may be implemented in an IMD 100 (FIG. 2) and housed in a common housing such as that shown in FIG. 2. Alternatively, functional portions of the system shown in FIG. 3 may be housed separately. For example, portions of the therapy delivery system 224 could be integrated with IMD 100 or provided in a separate housing, particularly where the therapy delivery system includes drug delivery capabilities. In this case, response module 218 may interact with therapy delivery system 224 via an electrical cable or wireless link.

Figure 4:
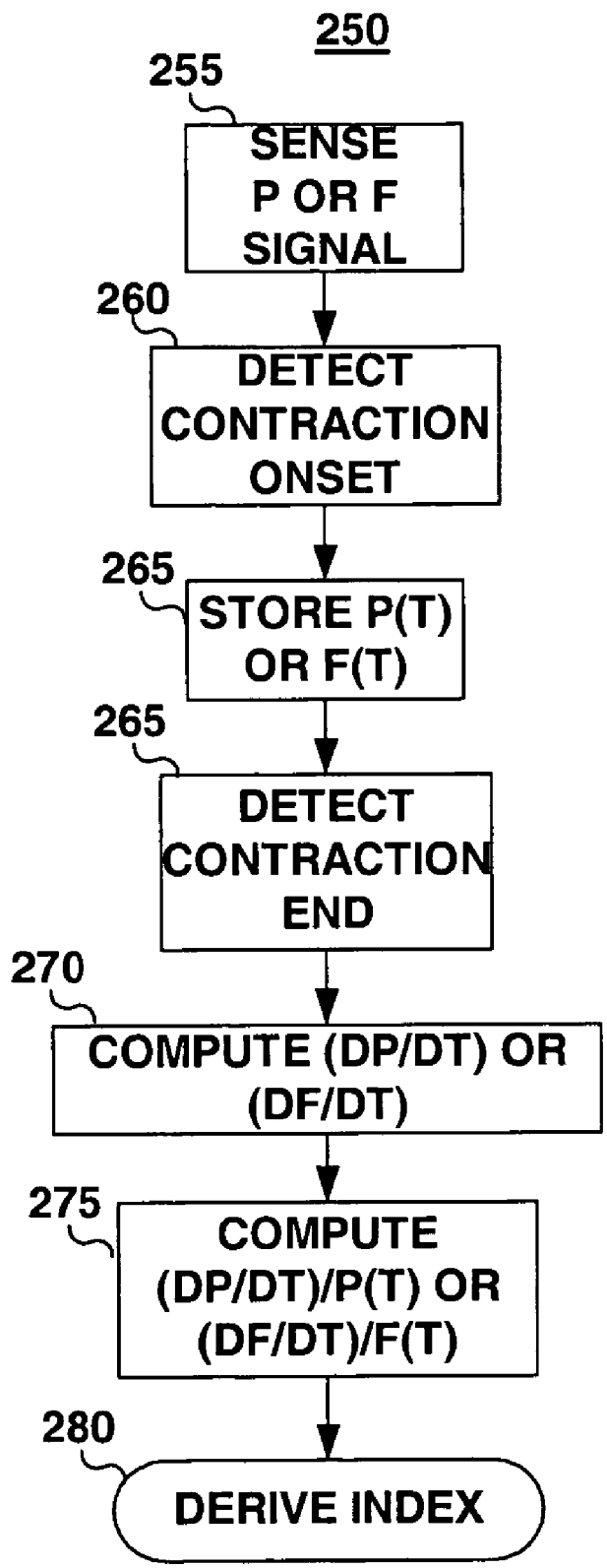
FIG. 4 depicts a flow chart summarizing a general method for computing a muscle function index from a pressure or force signal.

FIG. 4 is a flow chart summarizing a general method 250 for computing a muscle function index from a pressure or force signal. Pressure or force signal acquisition for muscle function monitoring may be enabled upon detecting predetermined triggering events, on a scheduled basis, or manually by a clinician, patient or other caregiver using an external device. When muscle function monitoring is enabled, the pressure or force signal is sensed at step 255. At step 260, the onset of a contraction is detected which triggers the storage of the pressure or force signal at step 265. The onset of a contraction may be determined according to a rise in the sensed pressure or force signal or according to other physiological signals or timing events that indicate a contraction is imminent. In the case of cardiac events, the onset of ventricular myocardial contraction can be detected based on R-wave detection from an EGM/ECG signal. The onset of atrial myocardial contraction can be detected based on P-wave detection. In other muscle monitoring applications, a depolarization signal on an EMG signal may be detected at step 260 to mark the onset of a contraction. Determination of a muscle function index may be made in response to a delivered stimulation pulse in which case the stimulation pulse may be used as a marker of contraction onset at step 260.

The pressure or force signal is stored in a memory buffer at step 265 during the contraction duration or at least a portion of the contraction duration which includes an isovolumic or isometric portion of the contraction. Alternatively, the pressure or force signal is acquired during at least a portion of the relaxation phase of a contraction cycle. The pressure or force signal may be suitably recorded for a desired duration of time or until the end of the contraction or contraction phase is detected at step 265 (or a relaxation or relaxation phase). For example, in myocardial function monitoring, a pressure signal may be acquired for a predefined interval of time, e.g., 500 ms, following R-wave detection. Alternatively, the pressure signal may be acquired starting at R-wave detection and ending upon detection of the end of the isovolumic contraction phase, the end of the ejection phase, the end of systole (valve closure), or at the end of the myocardial relaxation phase. These events may be determined according to times relative to EGM signal features, features of the pressure signal, heart sounds, or other cardiac signals. During skeletal muscle function monitoring, the force signal or an intramuscular pressure signal may be acquired starting when the signal crosses a predefined threshold and ending when the signal again crosses the same threshold or another threshold or may be timed relative to the delivery of a muscle or nerve stimulation pulse or detection of depolarization and repolarization signals on an EMG.

After acquiring the pressure or force signal for the desired interval of time, the first time derivative of the signal is computed at step 270. At step 275, the instantaneous stiffness ratio, $\dot{E}/E(t)$, is computed as the ratio of the first time derivative of the pressure or force signal to the corresponding instantaneous pressure or force:

$$\dot{E}/E(t) = \{dP(t)/dt\}/P(t)$$

Alternatively, the instantaneous stiffness ratio may be computed as the first time derivative of the logarithm of P(t) or F(t). In some embodiments, the end-diastolic pressure (EDP) may be subtracted from P(t) in the above computation such that the pressure evaluated is only the actively generated pressure. As such in an alternative embodiment, the ratio may be computed as:

$$\dot{E}/E(t) = d(\log(P(t)-\text{Ped}p))/dt$$

The instantaneous stiffness ratio $\dot{E}/E(t)$ has units of $s^{-1}$ and quantifies the number of strong bonds formed per unit time during actomyosin interaction. These bonds are formed and maintained with the action of calcium ions, and the rate of strong bond formation corresponds to calcium ion concentration. Thus, the peak $\dot{E}/E(t)$ measured during a contraction is the peak rate of strong bond formation and is correlated to the peak calcium ion transient.

A muscle function index is derived from the computation of $\dot{E}/E(t)$ at step 280. In one embodiment, the muscle function index is determined as the peak of $\dot{E}/E(t)$. Alternatively, a muscle function index is determined as the width or duration of the $\dot{E}/E(t)$ waveform, the integral of $\dot{E}/E(t)$, the positive or negative slope of the $\dot{E}/E(t)$ waveform, or another feature of the $\dot{E}/E(t)$ waveform. The time integral of $\dot{E}/E(t)$ will be a unitless value and corresponds to the number of strong bonds formed over the integration interval.

The derived index may be stored and averaged over a number of contraction cycles to determine a mean index or other statistical analysis may be performed. Trends in the index may be monitored to detect changes in muscle function. Changes in muscle function detected according to the muscle function index derived at step 280 can be responded to appropriately as described above for monitoring or therapy delivery purposes.

Figure 5A:
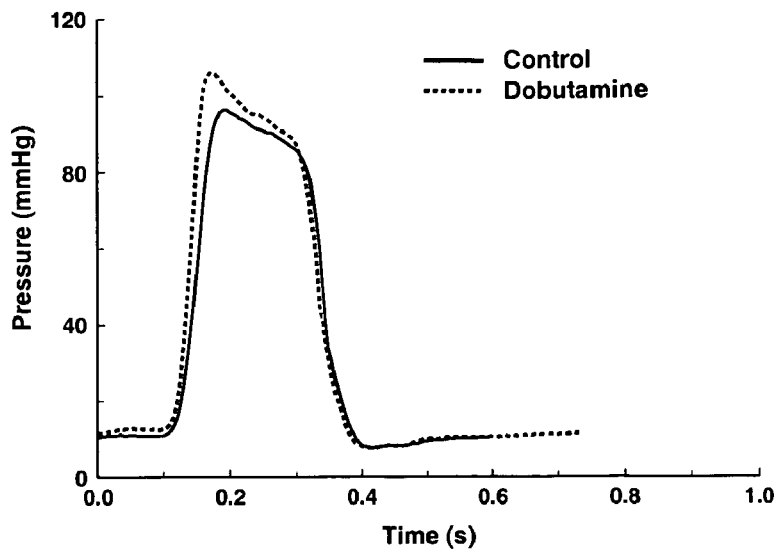
FIG. 5A shows time plots of left ventricular pressure waveforms obtained during a canine study under normal conditions and after Dobutamine infusion.
Figure 5B:
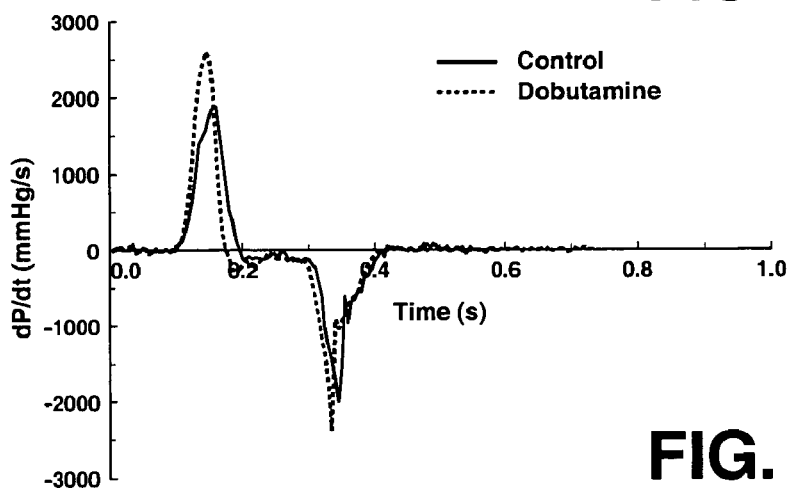
FIG. 5B shows the first time derivative of the pressure waveforms shown in FIG. 5A for control conditions and the Dobutamine intervention.

FIG. 5A shows time plots of left ventricular pressure waveforms obtained during a canine study under normal conditions and after Dobutamine infusion. Left ventricular (LV) pressure generated under a normal control condition is shown as the solid line. LV pressure generated after Dobutamine infusion is shown as the broken line. FIG. 5B shows the first time derivative of the pressure waveforms shown in FIG. 5A for control and the Dobutamine intervention. Dobutamine infusion is seen to increase both the peak pressure and the peak dP/dt, which would appear to be an enhancement of myocardial function. However, Dobutamine can also alter heart rate such that the changes in pressure and dP/dt can be due to changes in preload and afterload rather than changes in the inotropic state of the myocardium. In order to observe the effect of Dobutamine on the inotropic state of the muscle, the instantaneous stiffness ratio, $\dot{E}/E(t)$, is computed.

Figure 5C:
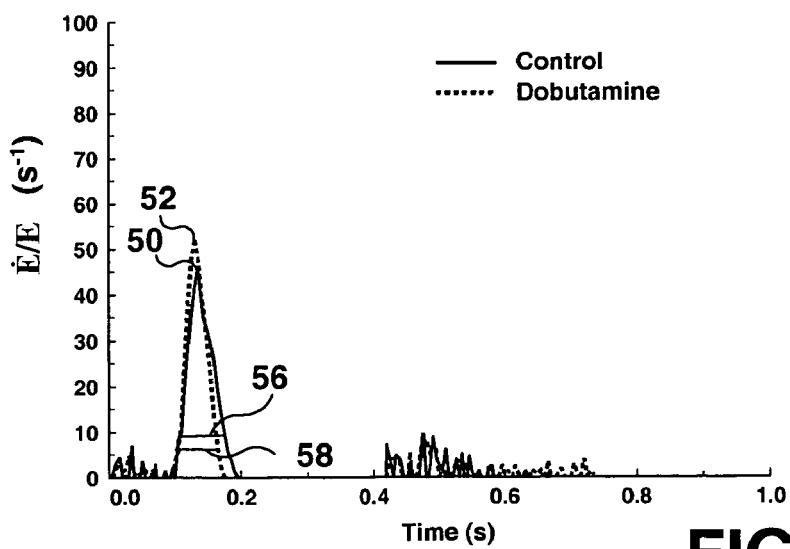
FIG. 5C shows the time plot of the instantaneous stiffness ratio, $\dot{E}/E(t)$, computed from the control and Dobutamine pressure waveforms shown in FIG. 5A.

FIG. 5C shows the time plot of $\dot{E}/E(t)$ computed from the control and Dobutamine pressure waveforms shown in FIG. 5A. $\dot{E}/E(t)$ will have units of 1/s and represents the rate of strong bond formation during actomyosin interaction. In accordance with the present invention, an index of muscle function is derived from the $\dot{E}/E(t)$ waveform. In one embodiment, the peak of the $\dot{E}/E(t)$ waveform is selected as the derived muscle function index. Alternatively, the duration of the $\dot{E}/E(t)$ waveform, a positive or negative slope, or the integral of the waveform may be derived as the muscle function index. In some embodiments, multiple features of the $\dot{E}/E(t)$ waveform may be derived as muscle function indices to be evaluated collectively for assessing muscle function changes.

Comparison of the waveforms shown in FIGS. 5A, 5B and 5C illustrate the usefulness of the muscle function index derived from $\dot{E}/E(t)$. In both FIGS. 5A and 5B, the effect of Dobutamine on peak pressure and peak dP/dt is seen to increase LV function. However, in FIG. 5C, the effect of Dobutamine on the inotropic state of the muscle is seen to be less dramatic than the effect on the pressure or dP/dt as evidenced by the similarity of the control (solid line) and Dobutamine intervention (broken line) $\dot{E}/E(t)$ waveforms. The difference in the control peak $\dot{E}/E(t)$ 50 and the Dobutamine intervention peak $\dot{E}/E(t)$ 52 is not proportional to the difference in the control dP/dt max and the Dobutamine intervention dP/dt max seen in FIG. 5B. The width 56 of the control $\dot{E}/E(t)$ waveform is only slightly greater than the width 58 of the $\dot{E}/E(t)$ waveform after Dobutamine infusion. These results suggest that in this experiment the effect of Dobutamine infusion on the inotropic state of the muscle is only a small contribution to the overall change in peak pressure and dP/dt max. In particular, the effect of Dobutamine on the calcium transient and the rate of strong bond formation is small based on an index derived from $\dot{E}/E(t)$.

In past practice, assessments of cardiac contractility have used an empirically selected pressure and/or cardiac volumes for normalizing dP/dt and have compared ratios, for example, of the maximum dP/dt to the empirically selected pressure under varying conditions. Such comparisons assume the force-length relationship is a linear relationship. Empirical selection of a pressure for normalization of dP/dt in assessment of ventricular contractility will result in empirical selection of a single point on the $\dot{E}/E(t)$ waveform. Empirical selection of a point on the $\dot{E}/E(t)$ waveform will not provide a consistently reliable reflection of a change in inotropic state. Changes in the maximum rate of strong-bond formation and the calcium transient will be reflected in changes in the peak $\dot{E}/E(t)$. Changes in the inotropic state of the myocardium will affect the $\dot{E}/E(t)$ waveform which can be measured by changes in peak $\dot{E}/E(t)$ or be measured by changes in the waveform width, slope, area, etc. Therefore, an index determined from the $\dot{E}/E(t)$ waveform will provide a more reliable measure of muscle function. The peak $\dot{E}/E(t)$ representing the peak rate of strong bond formation occurs earlier than the peak pressure and peak dP/dt, as can be seen in FIGS. 5A, 5B, and 5C. As such, empirical selection of the peak dP/dt or peak pressure for use in myocardial assessment will miss the peak $\dot{E}/E(t)$ and therefore not capture changes in the peak rate of strong bond formation.

Evaluation of $\dot{E}/E(t)$ waveform does not assume a linear force-length relationship. The muscle tissue is an elastic body having changing force-length relationships over time during a contraction cycle. By normalizing dP/dt by the instantaneous pressure P(t) and evaluating this ratio over the isovolumic or isometric contraction phase, the non-linearity effects of the force-length relationship are removed. One or more features of the $\dot{E}/E(t)$ waveform selected as a muscle function index will reflect changes in inotropic state, independent of afterload and preload changes.

Figure 6A:
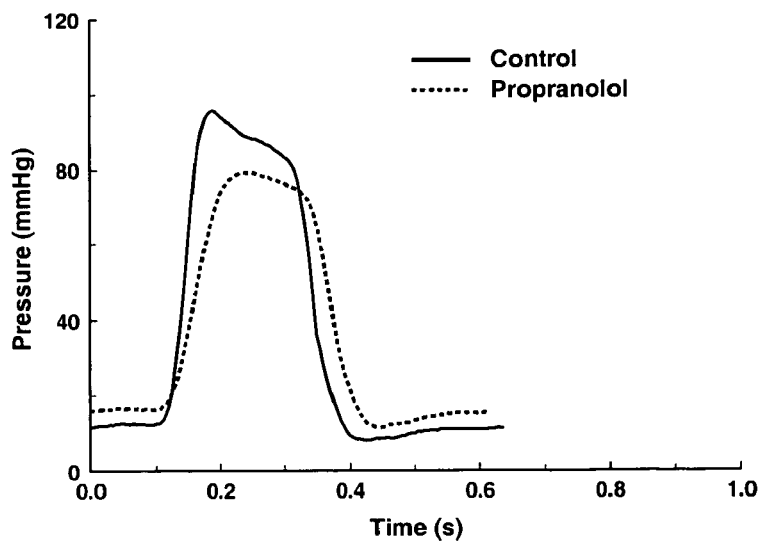
FIG. 6A shows time plots of left ventricular pressure waveforms obtained during a canine study under normal conditions and after Propranolol infusion.
Figure 6B:
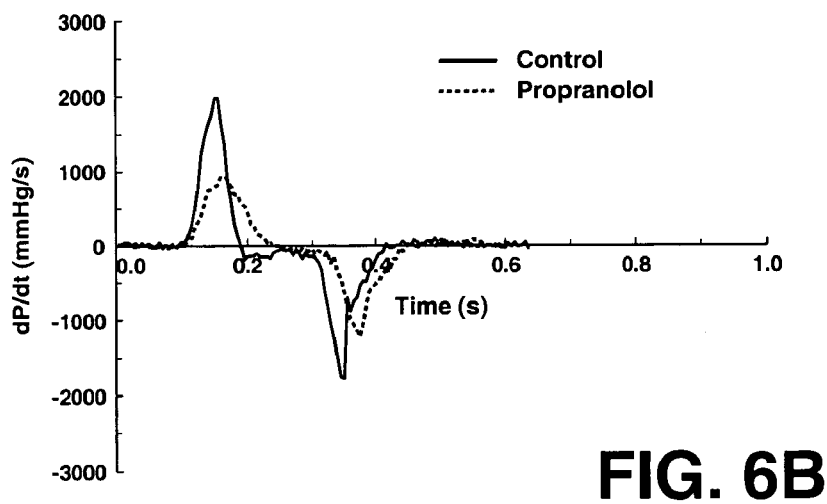
FIG. 6B shows the first time derivative of the pressure waveforms shown in FIG. 6A for the control conditions and the Propranolol intervention.

FIG. 6A shows time plots of left ventricular pressure waveforms obtained during a canine study under normal conditions and after Propranolol infusion. Left ventricular (LV) pressure generated under a normal, control condition is shown as the solid line. LV pressure generated after Propranolol infusion is shown as the broken line. FIG. 6B shows the first time derivative of the pressure waveforms shown in FIG. 6A for the control condition and the Propranolol intervention. Propranolol infusion results in a large decrease in peak pressure compared to control, as observed in FIG. 6A, and in maximum dP/dt as observed in FIG. 6B. Propranolol intervention causes the times of peak pressure generation and maximum dP/dt to occur later compared to control.

Figure 6C:
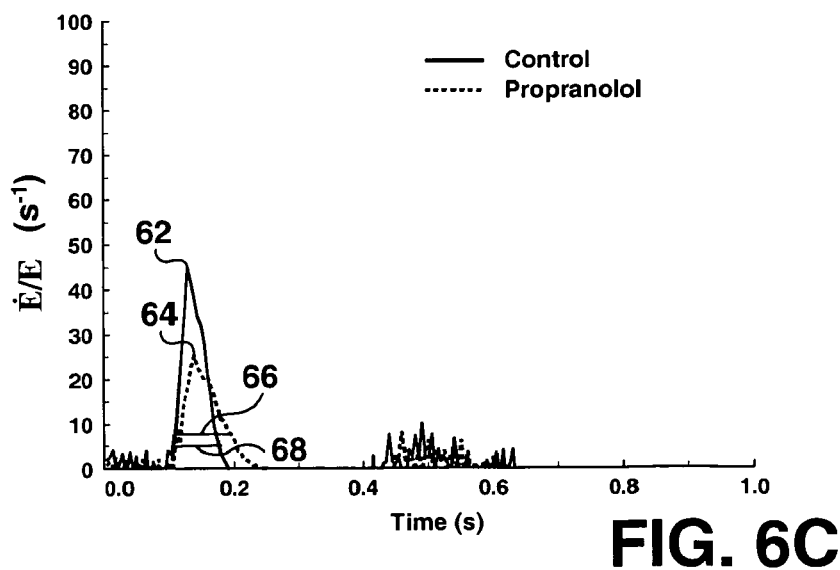
FIG. 6C shows the instantaneous stiffness ratio, $\dot{E}/E(t)$, waveforms computed from the control pressure waveform and the Propranolol intervention pressure waveform shown in FIG. 6A.

FIG. 6C shows the $\dot{E}/E(t)$ waveforms computed from the control pressure waveform and the Propranolol intervention pressure waveform shown in FIG. 6A. The $\dot{E}/E(t)$ waveform after Propranolol intervention (broken line) has changed remarkably from the control $\dot{E}/E(t)$ waveform (solid line). The Propranolol intervention peak $\dot{E}/E(t)$ 64 is substantially less than the control $\dot{E}/E(t)$ peak 62. As such, an index suitably selected as the $\dot{E}/E(t)$ waveform peak will reflect a decrease in the rate of strong bond formation in response to Propranolol infusion. Other features of the $\dot{E}/E(t)$ waveform will also reflect a change in the inotropic state of the myocardium. The Propranolol intervention $\dot{E}/E(t)$ width 68 is greater than the control $\dot{E}/E(t)$ width 66.

Note that the time of the Propranolol intervention peak $\dot{E}/E(t)$ 64 occurs at relatively the same time as the control peak $\dot{E}/E(t)$ 62. Both the peak pressure (FIG. 6A) and the peak dP/dt (FIG. 6B) are delayed following Propranolol infusion relative to the time of the control peak pressure and peak dP/dt. Consideration of the peak pressure (FIG. 6A) or peak dP/dt (FIG. 6B) for use in assessing myocardial contractility, in accordance with past practice, will result in empirical selection of points relatively later on the Propranolol intervention $\dot{E}/E(t)$ waveform than points selected on the control $\dot{E}/E(t)$ waveform. The peak rate of strong bond formation represented by the peak $\dot{E}/E(t)$ will not be captured in such an analysis. Derivation of a muscle function index from the $\dot{E}/E(t)$ waveform computed from the sensed pressure signal provides a more reliable assessment of muscle function, independent of non-linear preload and afterload effects.

The examples shown in FIGS. 5A, 5B, 5C and FIGS. 6A, 6B, and 6C relate to left ventricular myocardial function assessment using left ventricular pressure signals. A pressure signal obtained from within either the right or left ventricle is useful in assessing global myocardial function using an index derived from the instantaneous stiffness ratio computed from the right or left ventricular pressure signal. Aspects of the present invention may also be applied to the functional assessment of atrial myocardium using appropriate atrial pressure signals or any cardiac or papillary muscle in in vitro experiments using intramuscular pressure or force signals. It is recognized, that an instantaneous muscle stiffness ratio $\dot{E}/E(t)$ may alternatively be computed from a force signal obtained during skeletal muscle contraction for assessing skeletal muscle function, in situ or in vitro. Furthermore, intramuscular pressure signals may be useful in computing a muscle stiffness ratio $\dot{E}/E(t)$ for any striated muscle.

An instantaneous muscle stiffness ratio may be computed over any portion or all of an isovolumic or isometric contraction phase or over any portion or all of a relaxation phase. Indices of muscle function relating to relaxation properties (the dissociation of strong bonds and the sequestration of calcium) can be derived from selected features of the $\dot{E}/E(t)$ plot during the relaxation phase.

Thus, a system and method have been described which provide an index of muscle function derived from a pressure or force signal without requiring simultaneous volume or length measurements. Aspects of the present invention have been illustrated by the exemplary embodiments described herein. Numerous variations to these embodiments may be conceived by one having skill in the art and the benefit of the teachings provided herein. The described embodiments are intended to be illustrative of methods for practicing the invention and, therefore, should not be considered limiting with regard to the following claims.

We claim:

1. A method, comprising:
   sensing a pressure signal associated with a muscular contraction event via a chronically-implantable pressure sensor coupled to a chronically implanted medical device;
   computing an instantaneous stiffness ratio waveform as a ratio of a first time derivative of the pressure signal to an instantaneous pressure metric within said IMD; and
   deriving an index of muscle function from the instantaneous stiffness ratio waveform within said IMD,
   wherein the computing and deriving steps of said method are carried out within via operative circuitry wholly disposed within said IMD; and
   wherein the index of muscle function comprises a peak of the stiffness ratio waveform.

2. A method according to claim 1, wherein the pressure signal comprises a cardiac chamber pressure signal.

3. A method according to claim 1, wherein the muscular contraction event comprises at least part of one of a myocardial depolarization sequence and a myocardial repolarization event.

4. A method according to claim 1, wherein the pressure signal is obtained using an intracardiac pressure transducer.

5. A method according to claim 4, wherein the intracardiac pressure transducer is adapted to be disposed within a portion of a right ventricular chamber.

6. A method, comprising:
   sensing a force signal associated with a muscular contraction event, wherein the force signal is provided by a chronically-implantable sensor which is coupled to a chronically implanted medical device (IMD);
   computing an instantaneous stiffness ratio waveform as a ratio of a first time derivative of the force signal to an instantaneous force metric within the IMD; and
   deriving an index of muscle function from the stiffness ratio waveform within the IMD
   wherein the computing and deriving steps are performed via circuitry disposed within the. IMD; and
   wherein the index of muscle function comprises a peak of the stiffness ratio waveform.

7. A method according to claim 6, wherein the force signal comprises a cardiac chamber force signal.

8. A method according to claim 6, wherein the muscular contraction event comprises at least part of one of a myocardial depolarization sequence and a myocardial repolarization event.

9. A method according to claim 6, wherein the force signal is obtained using an intracardiac force transducer.

10. A method according to claim 9, wherein the intracardiac force transducer is adapted to be disposed within a portion of a right ventricular chamber.

11. A chronically implantable medical device (IMD), comprising:
    means for sensing a pressure signal associated with a muscular contraction event wherein the pressure signal is provided by a chronically-implantable sensor and said sensor couples to the (IMD);
    means within the IMD for computing an instantaneous stiffness ratio waveform as the ratio of the first time derivative of the pressure signal to the instantaneous pressure; and
    means within the IMD for deriving an index of muscle function as a feature of the instantaneous stiffness ratio waveform; and
    wherein the index of muscle function comprises a peak of the stiffness ratio waveform.

12. An apparatus according to claim 11, wherein the means for sensing the pressure signal comprises at least one fluid pressure transducer, and wherein the at least one fluid pressure transducer is adapted for deployment into fluid communication to a portion of the venous system of a subject.

13. A device according to claim 11, wherein the pressure signal comprises a cardiac chamber pressure signal.

14. A device according to claim 11, wherein the muscular contraction event comprises at least part of one of a myocardial depolarization sequence and a myocardial repolarization event.

15. A device according to claim 11, wherein the pressure signal sensing means comprises an intracardiac pressure transducer.

16. A method according to claim 11, wherein the intracardiac pressure transducer is adapted to be disposed within a portion of a right ventricular chamber.

17. A chronically implantable medical device (IMD), comprising:
    means for sensing a force signal associated with a muscular contraction event wherein the force signal is provided by a chronically-implantable sensor and said sensor couples to the (IMD);
    means within the IMD for computing an instantaneous stiffness ratio waveform as the ratio of the first time derivative of the force signal to instantaneous force; and
    means within the IMD for deriving an index of muscle function as a feature of the instantaneous stiffness ratio waveform; and
    wherein the index of muscle function comprises a peak of the stiffness ratio waveform.

18. A device according to claim 17, wherein the force signal comprises a cardiac chamber force signal.

19. A device according to claim 17, wherein the muscular contraction event comprises at least part of one of a myocardial depolarization sequence and a myocardial repolarization event.

20. A device according to claim 17, wherein the force signal sensing means comprises an intracardiac force transducer.

21. A method according to claim 17, wherein the intracardiac force transducer is adapted to be disposed within a portion of a right ventricular chamber.

* * * * *